United States Patent
Nilsson et al.

(10) Patent No.: US 10,423,453 B2
(45) Date of Patent: *Sep. 24, 2019

(54) DISTRIBUTED COMPUTATION SYSTEMS AND METHODS

(71) Applicant: INTERTRUST TECHNOLOGIES CORPORATION, Sunnyvale, CA (US)

(72) Inventors: Jarl Nilsson, Mountain View, CA (US); William Knox Carey, Mountain View, CA (US)

(73) Assignee: Intertrust Technologies Corporation, Sunnyvale, CA (US)

( * ) Notice: Subject to any disclaimer, the term of this patent is extended or adjusted under 35 U.S.C. 154(b) by 430 days.

This patent is subject to a terminal disclaimer.

(21) Appl. No.: 15/340,112

(22) Filed: Nov. 1, 2016

(65) Prior Publication Data

US 2017/0116035 A1    Apr. 27, 2017

Related U.S. Application Data

(63) Continuation of application No. 13/840,793, filed on Mar. 15, 2013, now Pat. No. 9,503,512.

(60) Provisional application No. 61/613,878, filed on Mar. 21, 2012.

(51) Int. Cl.
| | |
|---|---|
| G06F 15/16 | (2006.01) |
| G06F 9/50 | (2006.01) |
| H04L 29/08 | (2006.01) |
| G06F 9/48 | (2006.01) |
| G16H 10/60 | (2018.01) |

(52) U.S. Cl.
CPC .......... G06F 9/5011 (2013.01); G06F 9/4881 (2013.01); G06F 9/5066 (2013.01); H04L 67/10 (2013.01); G06F 2209/5017 (2013.01); G16H 10/60 (2018.01)

(58) Field of Classification Search
CPC . H04L 67/10; G06F 9/5066; G06F 2209/5017
See application file for complete search history.

(56) References Cited

U.S. PATENT DOCUMENTS

| | | | |
|---|---|---|---|
| 5,892,900 | A | 4/1999 | Ginter et al. |
| 6,157,721 | A | 12/2000 | Shear et al. |
| 7,430,585 | B2 | 9/2008 | Sibert |

(Continued)

FOREIGN PATENT DOCUMENTS

| | | |
|---|---|---|
| JP | 2002-014862 A | 1/2002 |
| JP | 2005-056201 A | 3/2005 |

(Continued)

OTHER PUBLICATIONS

Batheja et al.; "Adaptive Cluster Computing using JavaSpaces"; Proceedings of the 2001 IEEE International Conference on Cluster Computing, Oct. 11, 2001, pp. 323-330.

(Continued)

*Primary Examiner* — Yves Dalencourt
(74) *Attorney, Agent, or Firm* — Finnegan Henderson Farabow Garrett & Dunner LLP

(57) ABSTRACT

Systems and methods are described for performing distributed computations over a data set potentially owned or controlled by many stakeholders, each of whom may set their own policies governing access to and/or other use of their individual data.

23 Claims, 8 Drawing Sheets

(56) References Cited

U.S. PATENT DOCUMENTS

| | | | |
|---|---|---|---|
| 8,234,387 | B2 | 7/2012 | Bradley et al. |
| 8,544,103 | B2 | 9/2013 | Nilsson |
| 9,503,512 | B2 * | 11/2016 | Nilsson .................. H04L 67/10 |
| 2002/0010679 | A1 | 1/2002 | Felsher |
| 2004/0044648 | A1 * | 3/2004 | Anfindsen ............. G06Q 10/06 |
| 2004/0098447 | A1 | 5/2004 | Verbeke et al. |
| 2007/0180519 | A1 | 8/2007 | Boccon-Gibod et al. |
| 2007/0271381 | A1 | 11/2007 | Wholey et al. |
| 2008/0250227 | A1 | 10/2008 | Linderman et al. |
| 2008/0306872 | A1 | 12/2008 | Felsher |
| 2010/0047793 | A1 | 2/2010 | Toledo et al. |
| 2010/0057514 | A1 | 3/2010 | Chee et al. |
| 2011/0277991 | A1 | 11/2011 | Toledo et al. |
| 2012/0054280 | A1 | 3/2012 | Shah |
| 2012/0260346 | A1 | 10/2012 | Carey et al. |
| 2013/0060579 | A1 * | 3/2013 | Yu ......................... G06Q 10/06 705/3 |
| 2013/0160072 | A1 | 6/2013 | Reus et al. |

FOREIGN PATENT DOCUMENTS

| | | |
|---|---|---|
| JP | 2007-219634 A | 8/2007 |
| JP | 2008-176490 A | 7/2008 |
| JP | 2008-299527 A | 12/2008 |
| JP | 2011-045134 A | 3/2011 |

OTHER PUBLICATIONS

Callaway, E.; "Global Genomic Data-Sharing Effort Kicks Off"; Nature News, Mar. 6, 2014, pp. 1-2.

Chen et al., Extending Hadoop MapReduce to Support MPMD, Dec. 2011 (5 pages).

Gymrek et al.: "Identifying Personal Genomes by Surname Inference"; Science, vol. 339, No. 6117; Jan. 18, 2013, pp. 321-324.

Homer et al.; "Resolving individuals contributing trace amounts of DNA to highly complex mixtures using high-density SNP genotyping microarrays"; PLoS Genetics, vol. 4, No. 8, Aug. 2008, pp. 1-9.

Kolata, G.; "Poking Holes in Genetic Privacy"; New York Times, Jun. 16, 2013; pp. 1-3.

Lemke et al.; "Public and Biobank Participant Attitudes toward Genetic Research Participation and Data Sharing"; Public Health Genomics, vol. 13, Jan. 15, 2010, pp. 368-377.

Lunshof, J. et al.; "From Genetic Privacy to Open Consent"; Nature Reviews | Genetics, vol. 9, May 2008, pp. 406-411.

Matsunaga et al., "CloudBLAST: Combining MapReduce and Virtualization on Distributed Resources for Bioinformatics Applications," IEEE Fourth International Conference on eScience, Dec. 7-12, 2008, pp. 222-229.

Nyholt, D. et al.; "On Jim Watson's APOE status: genetic information is hard to hide"; European Journal of Human Genetics; vol. 17, No. 2; Feb. 2009; pp. 147-149.

Sankararaman, S. et al.; "Genomic privacy and limits of individual detection in a pool"; Nature Genetics; vol. 41, No. 9; Sep. 2009; pp. 965-967.

Tanaka, Y. et al., "Design and Implementation of Security Infrastructure of the GEO Grid"; 2008 Symposium on Advanced Computing Systems and Infrastructures (SACSIS), vol. 2008, No. 5, pp. 341-348 (Jun. 4, 2008).

International Search Report and Written Opinion dated May 15, 2013, for PCT Application No. PCT/US13/0331138, filed Mar. 20, 2013.

First Office Action and English translation dated Jun. 2, 2016 for Chinese Patent Application 201380026609.X, filed Mar. 20, 2013.

Extended European Search Report dated Aug. 3, 2016 for European Patent Application No. 13764399.5, filed Sep. 25, 2014.

Notice of Reasons for Refusal dated Mar. 15, 2017 and English translation for Japanese Patent Application No. 2015-501881.

Office Action dated Jun. 17, 2015, for U.S. Appl. No. 13/840,793, filed Mar. 15, 2013.

Office Action dated Jan. 25, 2016, for U.S. Appl. No. 13/840,793, filed Mar. 15, 2013.

Notice of Allowance dated Jul. 25, 2016, for U.S. Appl. No. 13/840,793, filed Mar. 15, 2013.

\* cited by examiner

DISTRIBUTED COMPUTATION SYSTEMS AND METHODS

CROSS REFERENCE TO RELATED APPLICATIONS

This application is a continuation of U.S. Application No. 13/840,793, filed Mar. 15, 2013, which claims the benefit of U.S. Provisional Patent Application No. 61/613,878, filed Mar. 21, 2012, all of which are hereby incorporated by reference in their entireties.

COPYRIGHT AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND AND SUMMARY

In distributed computing using multiple autonomous computers, various programming models such as MapReduce are used to increase processing speed and/or reduce processing time for computational problems. Such frameworks can be used for processing parallel problems across a large dataset using large numbers of computers or nodes, and are primarily employed to increase processing power by making use of a large number of relatively inexpensive computers. A limiting characteristic of distributed computing frameworks such as MapReduce is that they typically assume consistent access to data resources.

According to some embodiments, a distributed computing framework is described which can be used to solve computational problems where there is potentially inconsistent access to the data resources, such as where the various data resources are controlled according to different policies governing their access and/or use.

According to some embodiments a method for distributed computing over distributed digital data resources having differing associated rules is described. The method includes distributing a computing task that uses a plurality of distributed digital data resources by dividing the computing task into a plurality of sub-tasks to be performed by a plurality of distributed worker nodes including a first worker node having access to a first digital data resource, and a second worker node having access to a second digital data resource. The first digital data resource is associated with a first set of rules that correspond to conditions for accessing (and/or computations that can operate on) the first digital data resource. Similarly, the second digital data resource is associated with a second set of rules that correspond to conditions for accessing (and/or computations that can operate on) the second digital data resource. The conditions for accessing the first and second digital data resources can be different from each other. According to some embodiments, the method also includes performing the plurality of sub-tasks using the plurality of worker nodes on the plurality of digital data resources, each of the worker nodes thereby generating a partial result; and collecting and combining the partial results thereby forming a final result for the computing task.

According to some embodiments the rules associated with the data resources are determined at least in part by one or more stakeholders in the data resources, and the stakeholder(s) can subsequently alter the rules governing their access and use. According to some embodiments, the distribution of computational tasks is performed by an entity that may have the ability to request that computations be performed at multiple worker nodes, but that does not have direct access to the data resources managed by those worker nodes. In some cases, the worker nodes only have access to one or some of the data resources, which may be located in geographically separate locations, such as different towns, regions, or countries, in which regional or national policies governing access to and use of the data may vary. According to some embodiments, the rules are selected from a domain of possible rules that is not determined by the distributing entity.

According to some embodiments, rules are associated with data resources, governing access to and/or other use of the data resources. In other embodiments, rules can also (or alternatively) be associated with computations that operate upon the data resource in order to provide a specific view of the data resource. The computations may also be associated with a particular user or group of users in order to limit the user's or group's access to information contained in the data resource by requiring that at least one computation be applied to the digital data resource before revealing the information to the user or group. According to some embodiments, the association between the rules and the computations is made by creating a digitally signed document comprising a pairing of a unique representation of the digital data resource and a unique representation of the computations to be associated with the data resource. For example, in some embodiments, techniques are used such as those described in commonly assigned U.S. patent application Ser. No. 12/773,501, Policy Determined Accuracy of Transmitted Information, published as U.S. Patent Publication No. 2011/0277036 ("the '501 application"), which is hereby incorporated by reference in its entirety. In other embodiments, other techniques are used.

According to some embodiments the digital data resources include medical information stored in medical facilities, and at least some of the rules correspond to access conditions that protect patient privacy. According to some embodiments, the rules are set in part by the patients. According to some embodiments, the medical information may include some or all of genomic data, proteomic data, microbiomic data, and/or any other type of *-omic, medical, and/or healthcare-related data.

According to some embodiments, a method for distributed computing over distributed digital medical data resources having differing associated rules is described. The method includes distributing an executable (or interpretable) computer program or specification designed to operate on genomic and/or other medical data to a plurality of distributed worker nodes, including at least a first worker node having at least partial access to a first set of genomic and/or other medical data, and a second worker node having at least partial access to a second set of genomic and/or other medical data, the first set of data being associated with a first set of rules that correspond to one or more conditions for accessing the first set of data and/or computations that can operate on the first set of data, the second set of data being associated with a second set of rules that correspond to one or more conditions for accessing the second set of data, wherein at least some of the one or more conditions for accessing the first and second sets of data from the first and second sets of rules differ from each other.

BRIEF DESCRIPTION OF THE DRAWINGS

The inventive body of work will be readily understood by referring to the following detailed description in conjunction with the accompanying drawings, in which.

DETAILED DESCRIPTION

A detailed description of the inventive body of work is provided below. While several embodiments are described, it should be understood that the inventive body of work is not limited to any one embodiment, but instead encompasses numerous alternatives, modifications, and equivalents. In addition, while numerous specific details are set forth in the following description in order to provide a thorough understanding of the inventive body of work, some embodiments can be practiced without some or all of these details. Moreover, for the purpose of clarity, certain technical material that is known in the related art has not been described in detail in order to avoid unnecessarily obscuring the inventive body work.

Embodiments of the disclosure may be understood by reference to the drawings, wherein like parts may be designated by like numerals. The components of the disclosed embodiments, as generally described and illustrated in the figures herein, could be arranged and designed in a wide variety of different configurations. Thus, the following detailed description of various embodiments is not intended to limit the scope of the disclosure, as claimed, but is merely representative of possible embodiments. In addition, the actions in the methods disclosed herein do not necessarily need to be performed in any specific order, or even sequentially, nor need the actions be performed only once, unless otherwise specified.

Systems and methods are presented for performing distributed computations over a data set potentially owned or controlled by many stakeholders, each of whom has potentially set its own policies governing access to and use of its individual data.

Figure 1:
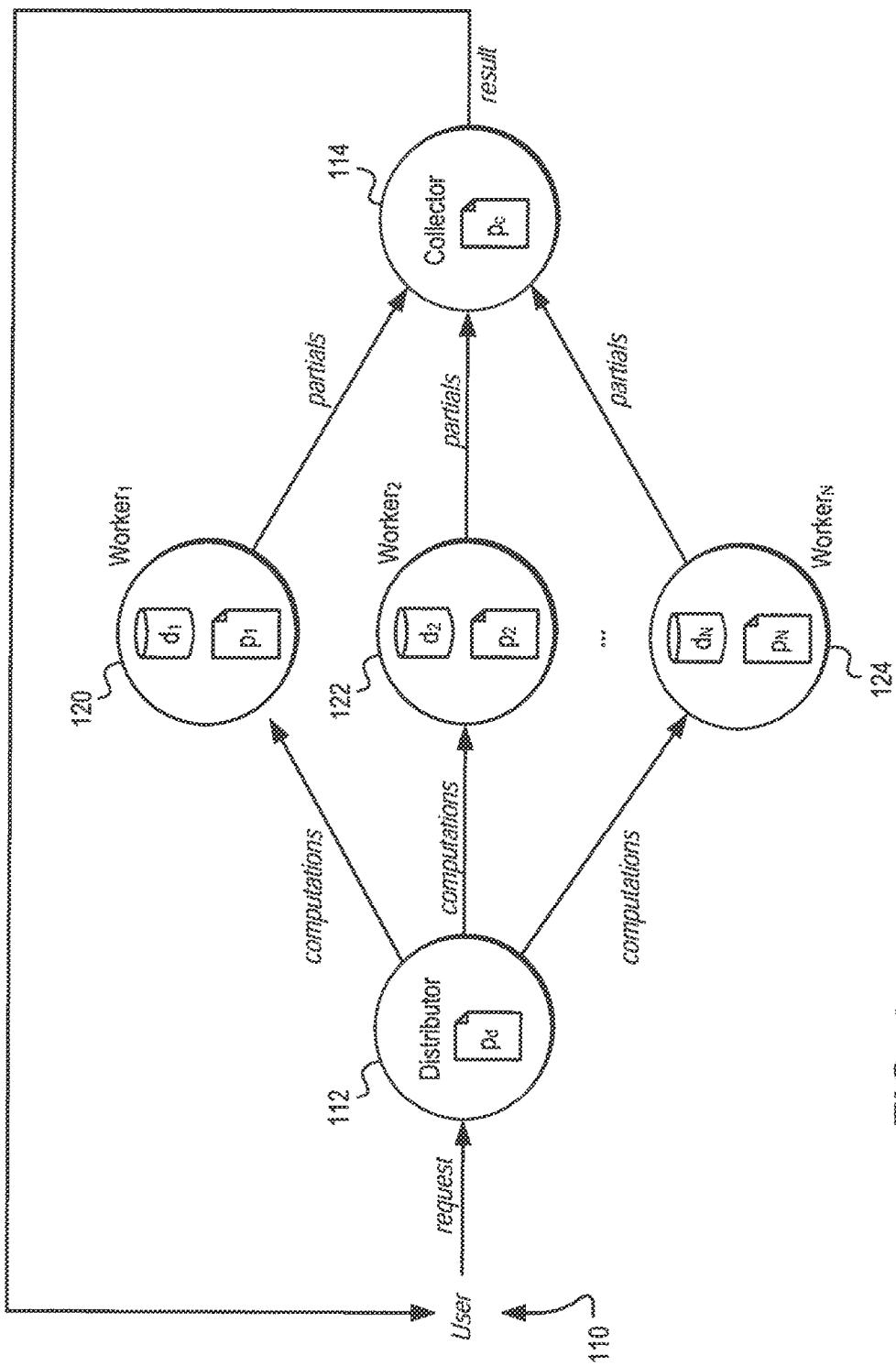
FIG. 1 shows an example data flow for performing distributed computations over a data set potentially owned or controlled by many stakeholders, according to some embodiments.

FIG. 1 shows an example data flow for performing distributed computations over a data set potentially owned or controlled by many stakeholders, according to some embodiments. The example data flow shown in FIG. 1 involves four main types of actors: User 110, Distributor 112, Workers (of which, example Workers 120, 122 and 124 are shown), and Collector 114. User 110 requests that a computation be performed and receives the result from the Collector 114. Distributor 112 divides the computation into a collection of sub-computations, each of which is potentially performed by a different Worker. Workers (for example, Workers 120, 122 and 124) are a collection of units that perform the sub-computations as directed by the Distributor 112. Collector (or Collator) 114 is the entity that collects the results of the various Workers and organizes them into a final form for consumption by the User 110.

As shown in FIG. 1, User 110 requests a computation to be performed over a set of distributed data. The work is divided by the Distributor 112 into individual work units, each of which is performed by a Worker (such as Workers 120, 122 and 124). A Collector 114 records and collates the intermediate results (partials), forming a final result to return to the User 110. Each actor potentially has a set of policies ($p_d$, $p_1$, $p_2$, $p_N$, $p_c$, etc.) that collectively govern the behavior of the computational system.

Unlike conventional systems, in some embodiments Workers are not assumed to have access (or the ability to gain access) to the same inputs or to otherwise interchangeably be able to reference the same data when directed to do so by Distributor 112. In addition, in some embodiments Workers can have their own policies related to the data—they need not operate solely under the direction of the Distributor 112. In addition, in some embodiments Collector 114 can do more than simply combine the outputs from the Workers into a final result to send to the User 110; instead, the Collector 114 can perform policy computations and persistently associate the result with a set of policies to be observed by the User 110. In some embodiments, policies at each stage of processing—User 110, Distributor 112, Workers (e.g. 120, 122 and 124), and Collector 114—are combined to derive a coherent result.

It will be appreciated that FIG. 1 (and the additional figures that follow below) has been provided for the sake of illustrating the various roles in a distributed computation system in accordance with some embodiments, and that a number of changes could be made without departing from the principles disclosed herein. For example, it will be appreciated that in some embodiments, some of the roles and/or actors illustrated in FIG. 1 (or in the figures that follow below) might be combined at least in part and performed by, or embodied in, a single entity or computer system, and/or further distributed amongst multiple entities and/or computer systems.

According to some embodiments, techniques described herein are applicable to situations in which there is not a single, consistent set of policies that govern the data processing required in a distributed computation. Polices may be distributed throughout the set of actors, and may be set independently by the data's stakeholders. In addition, it will often be desirable for policies to operate in the context of other policies. Some examples of the interactions between multiple policies are provided below, according to some embodiments.

Distributed Data Ownership. In contrast to some distributed computation systems, according to some embodiments, no assumption is made that the data are owned exclusively by and/or accessible to the Distributor 112, or shared between the Distributor 112 and all the Workers (e.g. 120, 122 and 124). Rather, in such embodiments it is assumed that each Worker controls or has access to a subset of the data in the system, and that each Worker potentially has its own policies governing access to this data.

According to some embodiments, a Worker or any other actor may enforce its policies in several ways, including, for example by: (1) applying policies at the point of request, and denying service to systems that cannot prove that they are authenticated or authorized for the given purposes according to the policy that obtains at the Worker; and/or (2) attaching policies to the data that they communicate with other actors, such that their policies may be enforced externally.

Credentials, Computations, and Context. According to some embodiments, at each stage of a distributed computation, any entity may be required to present appropriate credentials to be allowed to interact with other entities in the distributed system. For example, a User 110 may be required to authenticate to a Distributor 112 before the computations are even dispatched. Likewise, the Distributor 112 may be required to prove to the various Workers that it is a known, trusted entity. Similarly, in some embodiments a Collector 114 may accept partials only from trusted Workers.

According to some embodiments, credentials may follow the computation through the network such that actors further down the chain may inspect the origin of the computation, or the partial or the result. In other embodiments, the credentials associated with certain entities in the system may be stored in a database that is consulted by various actors in the computational network.

In many computational systems, secure authenticated channel (SAC) technologies like SSL/TLS provide both channel security and sender authentication. According to some embodiments, such protection is used in cases involving policy-managed distributed computations. However, according to some embodiments, there are additional requirements that may apply as well (or instead). For example, a Worker may want to validate the source of the sub-computations it is to perform. Such validations may happen inside the receiving Worker (e.g., after the channel security has been removed), which makes it desirable for the sub-computations to be individually signed (e.g., not just signed as part of the transport channel).

Likewise, according to some embodiments, in some situations it may not be sufficient to rely solely on a SAC for presentation of authentication credentials, since those credentials may need to also survive beyond channel setup and encryption/decryption if they are to be presented to third parties. For example, a Worker may need to prove to a Collector 114 that a particular work item was requested by a given Distributor 112, and that the Distributor 112 authenticated the requesting User 110, etc.

The context of each request may also be important in making policy decisions. Specifically, it will often be desirable for an actor in the system to know the intentions of the actors making requests of it in order to determine if particular actions or computations are to be performed. This might also be transitive—a Distributor 112 may communicate its intents to Workers, who in turn may communicate them to a Collector 114, possibly adding their own intents in the process. In some embodiments, intent may be context dependent. For example, a first party may make a decision about what to give a second party according to what the second party intends to do with the second party's result (e.g., the second party may have declared "I will send my result onward to Bob. Can I have information about Alice?"). This illustrates the transitivity of policy decisions according to some embodiments.

Data Privacy. According to some embodiments, Workers own their data in the sense that they manage access to and/or other use of particular data on behalf of entities that they represent. For example, a Worker might be a computational/storage unit at a particular hospital, which owns (or at least manages) the health records of patients at that hospital. A researcher conducting a survey may wish to query the Worker (in parallel with other Workers at other hospitals) to collect some statistics concerning its patients. For instance, a researcher might want to know how many female patients above the age of 85 have remained free of ovarian cancer.

According to some embodiments, the policies of the Worker (e.g. 120, 122 and 124)—which encode the policies of the hospital in this example case—will dictate what information, if any, can be provided to a Collector 114. Depending upon the specificity of the query, the Worker may wish to respond with the requested information, no information whatsoever, or even modified information. For example, some healthcare information systems randomize the results if they determine that too much personally identifiable information is being revealed by a given query; and/or by the history of queries that the Worker has revealed to a given Collector 114 or User 110; and/or by the overall amount of information that has been released concerning a given patient.

Applying Policy and Attaching Policy. According to some embodiments, Workers may, for example, forward one or both of the following different kinds of outputs on to a Collector: (1) a partial to which policies have already been applied at the point of service, in which case the Worker is implicitly trusting the Collector, User, etc. in their later uses of the information; and/or (2) a partial that persistently associates the result itself with a set of rules, keys, and/or computations (e.g., as described in commonly assigned Provisional Patent Application No. 61/474,212, filed Apr. 11, 2011, and U.S. patent application Ser. No. 13/444,624, filed Apr. 11, 2012, both entitled "Information Security Systems and Methods" each of which is incorporated by reference in its entirety herein) that will be used to enforce the policy as it flows downstream through the system. This approach relies on computational machinery downstream of the Worker that is capable of applying the rules and performing the associated computations.

In the latter case, a Collector 114 would receive policy-managed partials and would evaluate the rules as a prerequisite to computing the result.

The goal of the Collector (or Collator) 114, according to some embodiments, is to collect the partials returned by the Workers and combine them into a coherent response to provide back to the User 110. It will be appreciated that a variety of approaches could be used to evaluate the policies from the various Workers in such a scenario; four illustrative examples are described below.

1. If allowed under the policies associated with each partial, the Collector 114 evaluates the partials serially, including whatever information may be gleaned from each Worker into the final result computation.

2. If the policies associated with the partials require it, the Collector 114 evaluates the partials in context, providing the contextual information required by each partial's policy, which may include information about the other partials to be evaluated;

3. The Collector 114 packages the policy-managed partials into a second container (e.g., a digitally signed and/or encrypted electronic object)—possibly associated with its own policies and computations—that will be sent on to the User 110, effectively delegating the burden of computing the final answer to the User 110.

4. The Collector 114 selects a representative sample of the partials or policy managed partials to be packaged into the Collector container and returned to the User 110 for final evaluation.

According to some embodiments, an example of the second approach—policy evaluation in context—may occur when certain Workers do not wish to allow the partials that they provide to be combined with Workers operating in other institutions. For example, two Workers that are contributing partials to a final computation might be business adversaries. Their policies might disallow their partials to be combined with partials from certain Workers, or put more positively, only allow combination with partials from appropriately credentialed Workers. In some embodiments, the Collector 114 determines how to resolve potential policy conflicts without violating the Workers' policies.

According to some embodiments, a feature of some of the described frameworks is that the stakeholders in the data resources are able to change or alter the policies governing access to and/or other use of their data resources over time.

Several example use cases will now be described for purposes of illustration.

A network will now be described in accordance with some embodiments where stakeholders in data coexist with customers of that data. In some embodiments, the network can be public, such as the Internet, or private, such as a proprietary corporate network or a network owned and/or operated by a number of corporations, academic institutions, etc. as a shared resource for a project, and/or a combination thereof.

Figure 2:
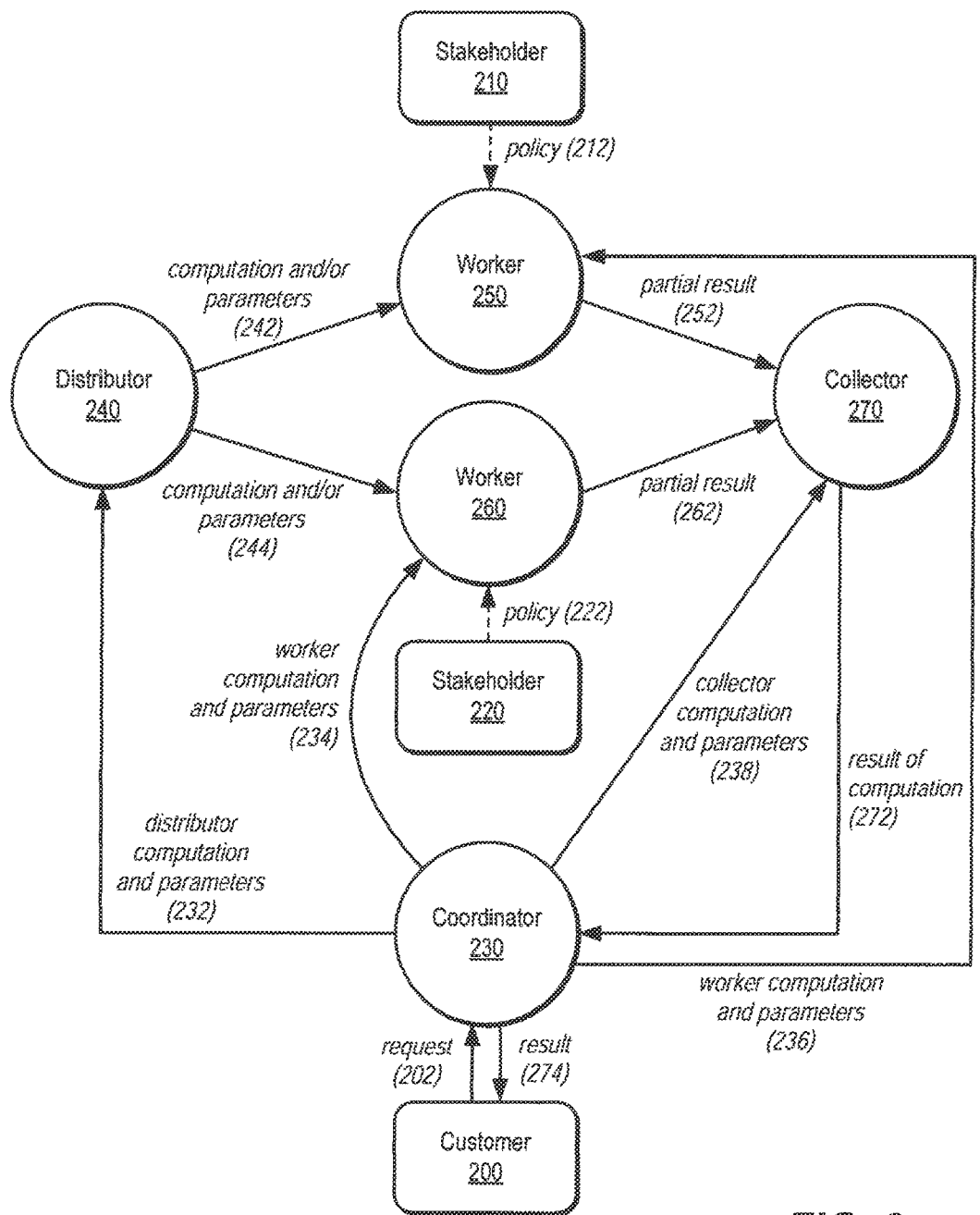
FIG. 2 is a diagram illustrating an example use case, according to some embodiments.

FIG. 2 is a diagram illustrating an example use case, according to some embodiments. In this example, a Customer 200 wants to perform a wide survey of data owned by multiple stakeholders, including at least two stakeholders 210 and 220. The data are stored in a distributed fashion, such that access to the data themselves are managed by Worker processes operating under the control and policies of the various stakeholders. Worker 250 is one such worker that governs access to data under policies 212 of stakeholder 210. At 202, the Customer 200 makes a computation request of a Coordinator 230. The Coordinator 230 will be responsible for orchestrating the distributed computation that incorporates information managed by the various stakeholders.

According to some embodiments, the Coordinator 230 effects the computation requested by Customer 200 by partitioning the computation into three sub-computations: one to be executed by the Distributor 240, one to be executed by the Workers 250 and 260, and one to be executed by the Collector 270. The computation 232, produced for the Distributor 240, is designed to partition the overall computational task among the various Workers and to send to each Worker a second computation (or parameters for a second computation) (e.g. 242, 244) designed to operate on the data managed by that Worker. The distributor computation 232 may include, for example, functionality that consults an index (or, e.g., a distributed hash table or the like) to determine the location of the data of interest and to distribute the computations or parameters 242 and 244 appropriately. According to some embodiments, the Distributor 240 creates computations to send to the various Workers using the computation 232 provided to Distributor 240 by Coordinator 230. In other embodiments, the Coordinator 230 sends the Worker computations directly to eligible Workers (e.g. 234, 236) and the Distributor 240 simply provides input parameters to those computations at, e.g., 242 and 244.

As noted above, the Coordinator 230 may send computations and parameters directly to Workers (e.g. 234, 236), or it may delegate this task to the Distributor 240. The Coordinator 230 also produces a computation and/or a set of parameters (238) for the Collector 270 that will combine the partial results produced by the Workers to yield a final result to return to Customer 200.

At 242 and 244, the Distributor 240 produces partial computations or parameters and sends them to Workers 250 and 260, respectively. Workers 250 and 260 then decide, according to policies 212 and 222 (produced, e.g., by stakeholders 210 and 220, respectively) whether to perform the computations at all. In general, the policy sets 212 and 222 will not be the same; the stakeholders 210 and 220 have potentially divergent interests in their data, and correspondingly different policies governing how their data may be accessed or used. It will also be appreciated that, in general, the activities of each Worker may be governed by the policies of several stakeholders, not just one. According to various embodiments, the decision to perform a computation at all may be made by various methods including, but not limited to some or all of the following: (a) examining the digital signatures over the computations 242 and 244 and determining whether those digital signatures were created by a trusted entity, (b) evaluating the purpose or intent of the request, as expressed by the Customer 200 and embodied in the computations 242 and 244 or the input parameters for these computations, (c) performing an analysis on the computations 242 and 244 in order to determine the risk they pose in terms of revealing private data, etc.

Assuming that Workers 250 and 260 decide to accept the computations 242 and 244, these computations are run over the data managed by Workers 250 and 260. During or after execution of the computations 242 and 244, the Workers may perform additional policy calculations that will govern how they should respond to the requests. Such computations may include a calculation of the amount of information that would be revealed by responding, which may depend on the amount of information already revealed about the data in question. These computations may also be based on how much information has been previously revealed to the Customer 200, or estimates of how easily a malicious party who intercepts the result can extract sensitive information. In some embodiments, the responses produced by running the computations may be constructed in several ways, including but not limited to some or all of the following: (a) by returning the result of the computation directly, (b) by returning nothing due to a conflict with the policies specified by a stakeholder (e.g. policies 212 and 222), (c) returning an error message indicating the policy conflict, an error in the programs, a runtime exception, etc., (d) returning a modified version of the computed result that makes it more difficult to infer or exploit the revealed information (specific methods may include adding random noise to the results, decreasing the resolution of the results, averaging the results with others, etc.), or (e) returning a derived resource, for example, a result that is securely and persistently associated with a specific computation, such that the computation must be run over the result before the result is revealed (e.g., as described in the '501 application). In some embodiments, these response strategies are evaluated by each Worker independently.

Referring once again to FIG. 2, each of the Workers that decide to provide a result for the requested computations sends its partial result (e.g. 252, 262) to a Collector 270. The Collector 270 combines the partial results together using the collector computation 238 to yield an answer 272 to the original computational request 202, which is then sent on to the Coordinator 230. At this point, the Coordinator may apply its own policies regarding how to respond to the Customer request, which may result in a response 274 that differs from the Collector response 272. The modifications that may be applied by the Coordinator could be similar to those applied at the Workers 250 and 260, described above.

According to some embodiments, the example case shown in FIG. 2 can be extended. Based on result 274, Customer 200 may determine that the results from the previous computation warrant further investigation. For example, it could be the case that there is a potential for profit if the data provided by Worker 250 and other stakeholders is made available to Customer 200 with higher precision. In a second request similar to that of 202, Customer 200 expresses his interest in the higher-precision data by, for example, offering increased payment. If the offer is acceptable according to the policy 212 of Worker 250, Worker 250 allows the earlier result provided to Customer 200 to be made available to Customer 200 with higher precision.

Figure 3:
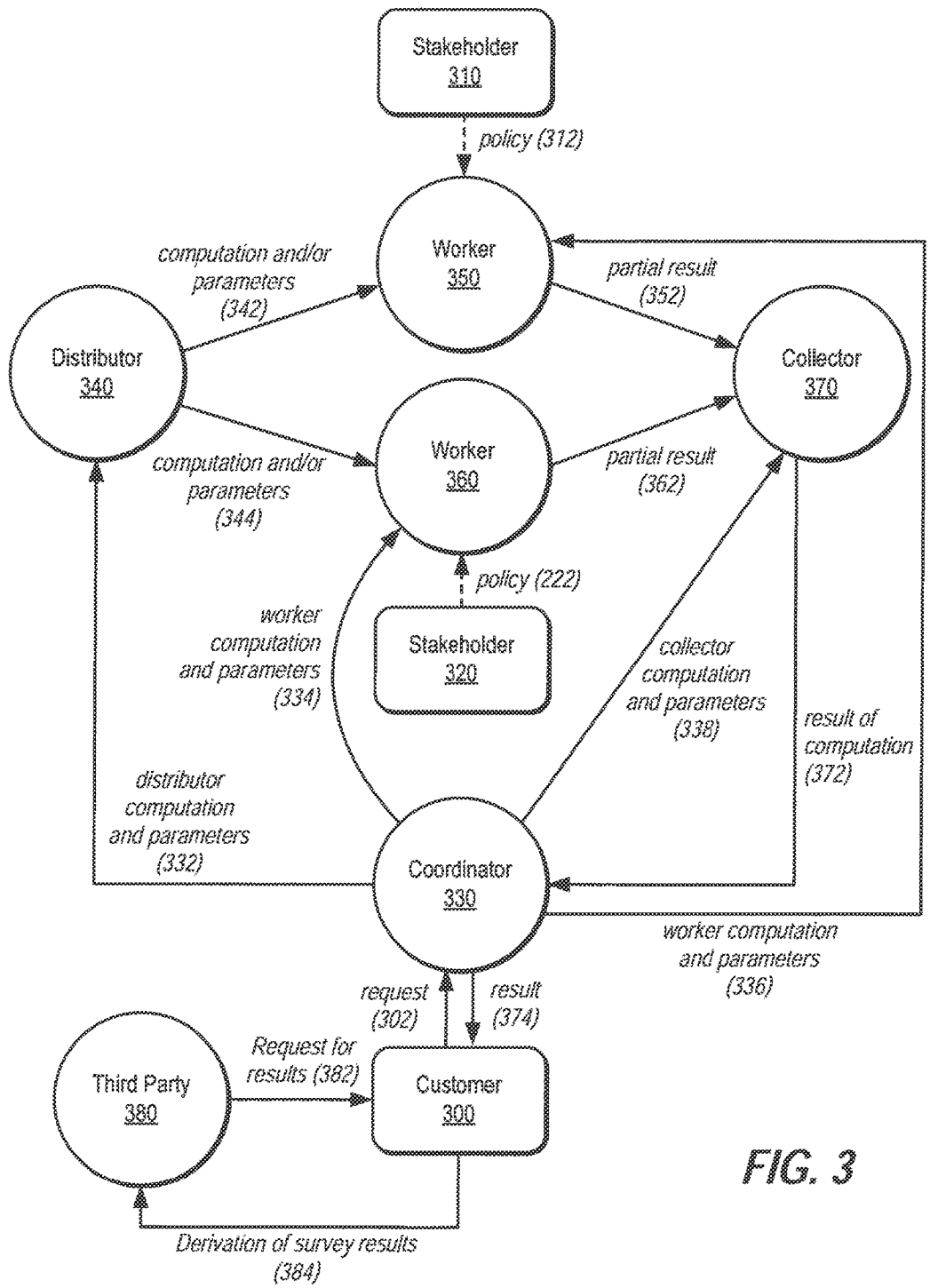
FIG. 3 is a diagram illustrating aspects of a another use case, according to some embodiments.

FIG. 3 is a diagram illustrating aspects of a third use case, according to some embodiments. In this example, Coordinator 330, operating on behalf of Customer 300, is conducting a survey over data governed by Worker 350, and other workers (including Worker 360). In this case, Coordinator 330 has a trust relationship with Worker 350, and other workers (including Worker 360) according to which raw data from the survey is freely returned to Coordinator 330 on the condition that Coordinator 330 creates derivations of the result enforcing the mutually agreed on policies if the result is provided to a third party. After the final result of the computation 372 is returned, Coordinator 330 makes the derivation of the result available to other researchers such as Third Party 380. The derivations enforce the policy of the stakeholders (including Coordinator 330 and Workers 350 and 360) in the third party researcher 380's calculations.

Figure 4:
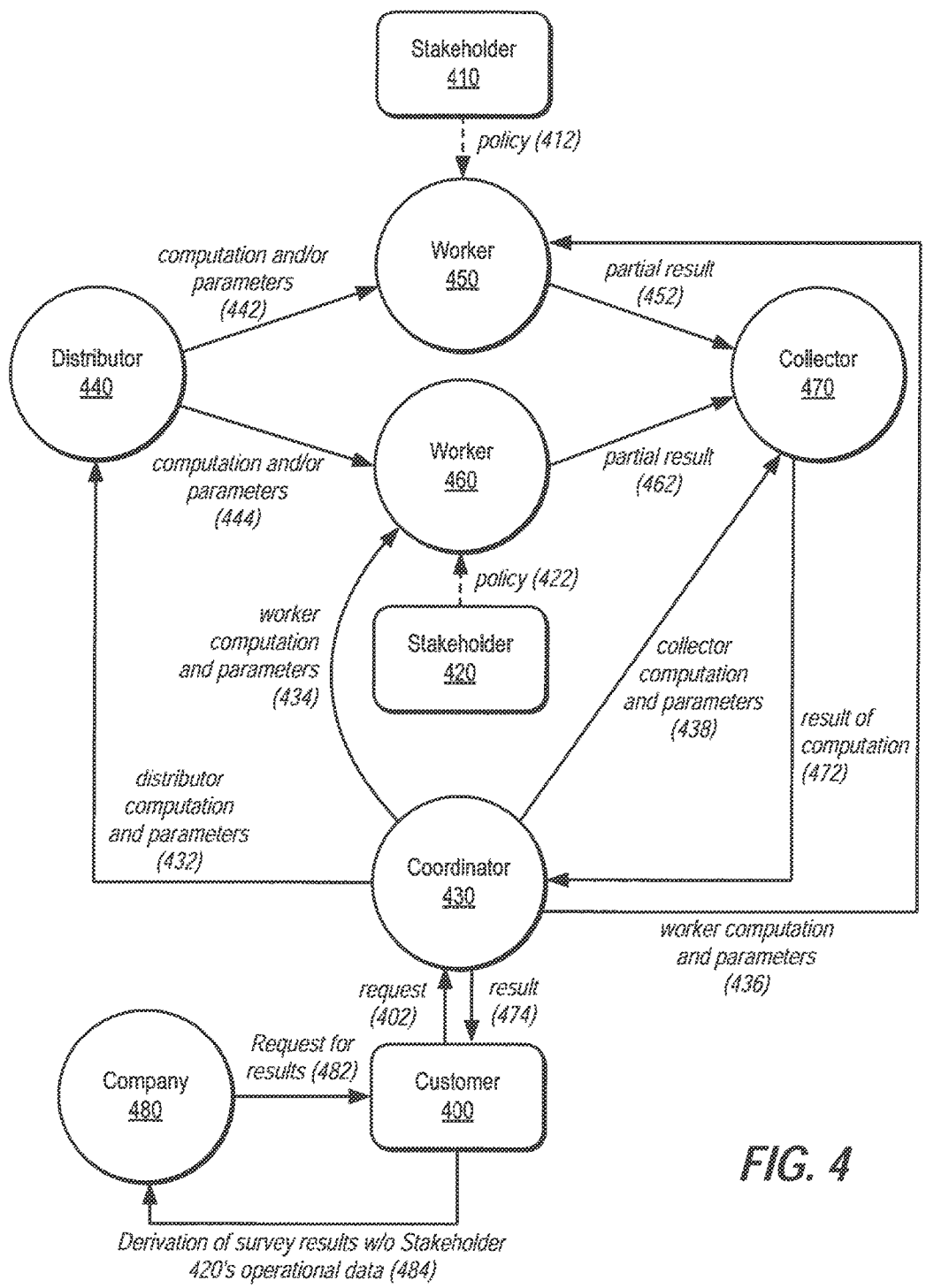
FIG. 4 is a diagram illustrating aspects of another use case, according to some embodiments.

FIG. 4 is a diagram illustrating aspects of a fourth use case, according to some embodiments. In this case Stakeholder 420 and Company 480 are competitors. Further, Stakeholder 420 has found it to be a competitive advantage to withhold the results of operations on his data from Company 480. While Coordinator 430 and/or Distributor 440 maps the survey computation out to the various workers without knowledge of or regard to the animosity between Stakeholder 420 and Company 480, Worker 460 attaches a policy rule to the derivation that prevents the result from the computation on Stakeholder 420's data to be used in conjunction with Company 480's data. According to some embodiments, due to Worker 460's attachment of Stakeholder 420's policy rule, either Collector 470 or Coordinator 430 has to make the choice of leaving Worker 460's data out of the survey results 484 altogether or returning to Company 480 a derivation that prevents the use of Stakeholder 420's data.

Figure 5:
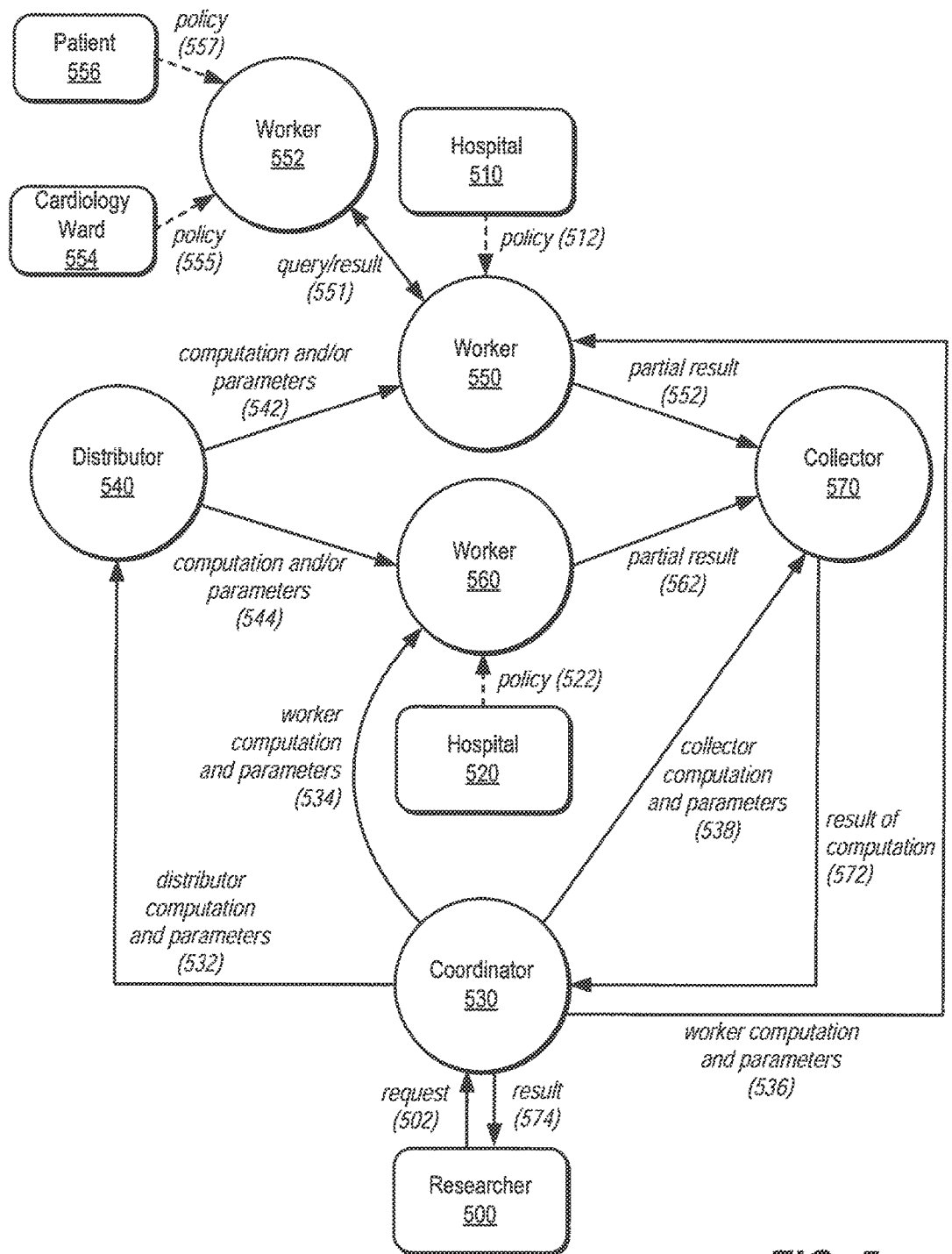
FIG. 5 is a diagram illustrating aspects of additional use cases, involving distributed queries of heath records, according to some embodiments.

FIG. 5 is a diagram illustrating aspects of a fifth use case, involving distributed queries of health records, according to some embodiments. In this example, it is assumed that several hospitals, including Hospitals 510 and 520 have put their medical data into digital form. Each hospital has its own policies (512 and 522), as well as in some cases individual policies negotiated with patients during diagnosis and sampling. Some policies are mutually exclusive, e.g., such that some patient policies prohibit participation in for-profit surveys, while the hospital allows for-profit surveys. Note that in general, the data resources may be distributed both administratively and geographically, due to access and ownership rights, security concerns and/or the sheer size of the data. For example, for medical data such as genomic data (which is also described in connection with FIG. 7), the data may be distributed due to ownership and/or privacy/security concerns of the patients and/or medical facilities, as well as due to the sheer size of the data resources and the corresponding costs of centralizing these resources.

Researcher 500 is a researcher from a for-profit pharmaceutical company and wishes to survey the newly available digital records. Researcher 500 connects to the Coordinator 530 and provides its credentials together with a survey. The Distributor 540 distributes the credentials and the queries to Workers 550 and 560 that manage the data (of Hospitals 510 and 520, respectively) to be queried in the survey. Worker 550 (which manages access to Hospital 510's data set) now creates a request (and in this sense acts as a distributor, or sub-distributor) to the different sub units (for example, the departments of Hospital 510). In this case the sub-units include the Cardiology Ward 554 and possibly a number of other wards. Patient 556 is an aging, but otherwise healthy former heart patient who has attached a policy 557 to her records with the Cardiology Ward that allows her data to be used only in surveys endorsed as non-profit by the American Heart and Lung Association. Patient 556's data is therefore withheld from Worker 550, Collector 570, and Coordinator 530, and her result is not included in the larger cross-hospital survey.

According to some embodiments, a sixth use case, involving distributed computations and degraded partials, will be described with respect to FIG. 5. In this example, Researcher 500 has discovered a new valuable pharmaceutical treatment. In order to test this treatment, Researcher 500 needs to survey males from a particular demographic being between 170 cm and 190 cm in height and having been infected with a certain virus and living in a certain geographic region. The Hospitals 510 and 520 in the survey area each have a policy against responding to surveys in a manner that reveals personally identifiable information (and/or the countries in which the hospitals operate may have laws to that effect). At the various Workers (e.g. 550 and 560), each set of hospital-specific results are investigated in the context of the survey. In this example, only a single patient record matches the survey criteria at Worker 550. Since only one patient record has been found that meets the criteria, a survey result with lower resolution data (or alternatively, a derivation that associates a resolution-decreasing computation with the result), is presented to Collector 570 and thence Researcher 500.

According to some embodiments, an example of a type of policy associated with medical data resources is a policy that prevents or deters unsolicited commercial content messages (such as targeted spam emails) that otherwise may result from access to a patient's medical data. For example, if the medical data indicates a patient having a likelihood of diabetes, then commercial third-parties may wish to target that patient with diabetes treatment or prevention products. The patient or hospital can add a type of policy that prevents or deters such access and/or resulting unsolicited messages.

According to some embodiments, another example of a type of policy associated with medical data is a policy that prevents the data from leaving a particular geographic region. For example, a particular country may have a national law that prevents certain types of medical data from leaving the country without express written consent of the patient. According to some embodiments, the techniques described herein can be applied to gather information in such a situation. For example, a researcher may prepare a survey computational algorithm that is sent to hospitals in various countries, performs the data processing on the medical data directly at those locations, and then sends back the results (or partial results) which do not include any patient identifying information (which, for example, may be a condition set by some policies in some locations).

Note that in general there may be more than one stakeholder in a data resource. In the example of medical records at a hospital, the hospital is typically a stakeholder, as well as each of the patients from whom the data was collected. Note also that in some cases the policies are set by the hospital alone, but in other cases policies are set wholly or in part by one or more of the data's other stakeholders (e.g., the example of the Patient and Cardiology Ward described above in connection with FIG. 5). According to some embodiments, one or more of the stakeholders may have a policy that the data resource can only be used if certain monetary compensation, or other compensation, is made.

Figure 6:
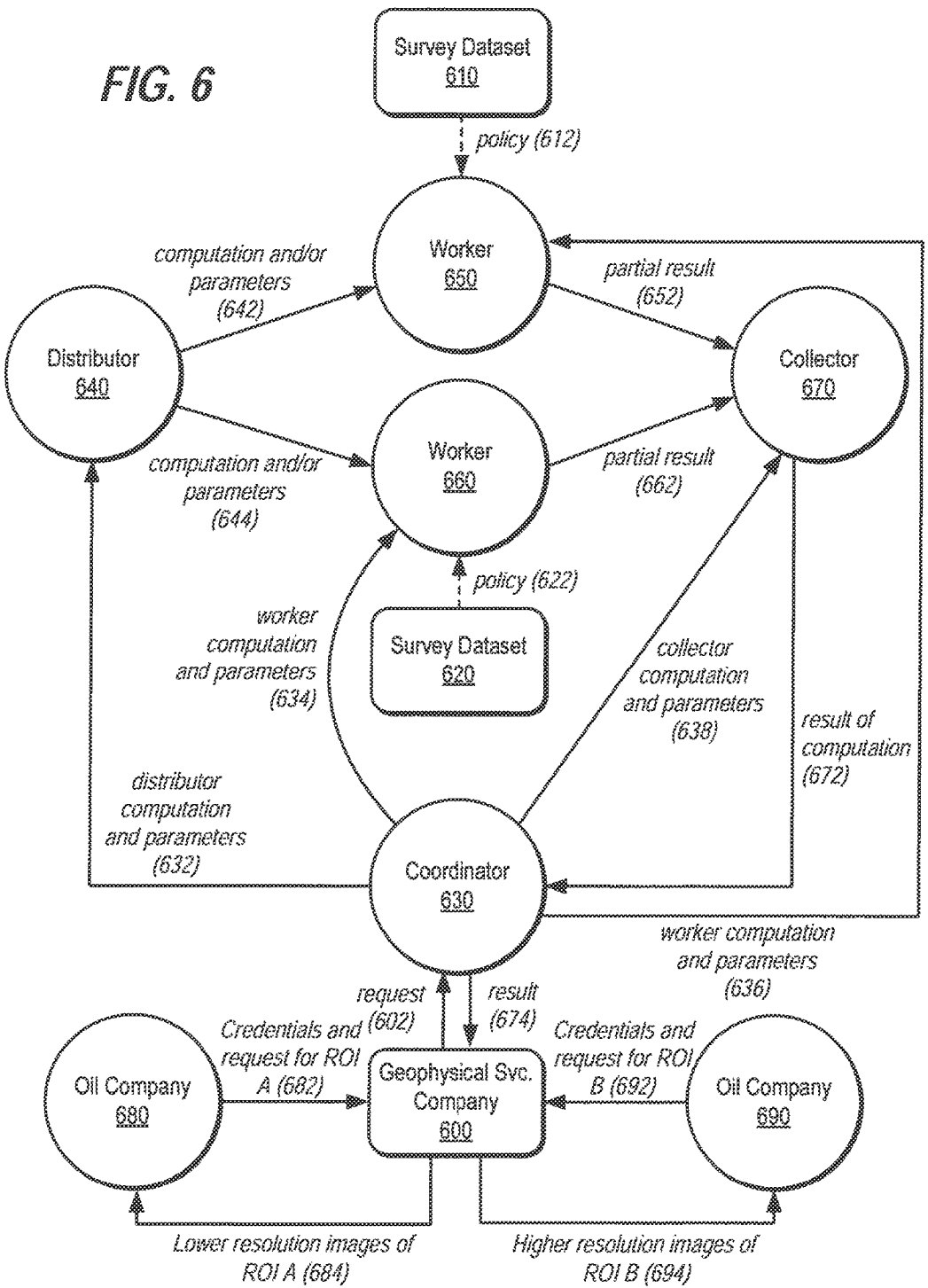
FIG. 6 is a diagram illustrating aspects of another use case, involving oilfield seismic data, according to some embodiments.

FIG. 6 is a diagram illustrating aspects of a seventh use case, involving oilfield seismic data, according to some embodiments. In this example, seismic data for possibly hydrocarbon-bearing subterranean regions of interest is distributed among several seismic survey datasets including 610 and 620. Geophysical Services Company 600 has ownership rights in, or has other access rights to, each of the datasets 610 and 620. In this example, the Geophysical Services Company 600 has exclusive ownership of dataset 620, but dataset 610 is co-owned with an Oil Company 690 due to partial funding of the acquisition costs of that dataset by Oil Company 690. Oil Company 690 has negotiated a condition that the highest resolution results (or, in some embodiments, derivations) based on dataset 610 will not be provided to direct competitors of Company 690. Accordingly, dataset 610 includes a policy 612 to that effect. Oil Company 680, which is a direct competitor to Oil Company 690, requests seismic imaging data for use in evaluating a region of interest ("ROI A") which includes some of the survey dataset 610. As a result of the policy on dataset 610, a lower resolution imaging product is delivered to Oil Company 680. However, when Oil Company 690 makes a request for seismic imaging data for use in evaluating another region of interest (ROI B), which also includes some of the dataset 610, a higher resolution imaging product is delivered to Oil Company 690. According to some embodiments, different levels of resolution or other quality measures can be provided depending on price and/or other factors. For example, the Oil Company 680 might develop a new, higher-quality processing algorithm, with which it can sell or re-sell higher quality results to one or more of its customers.

Figure 7:
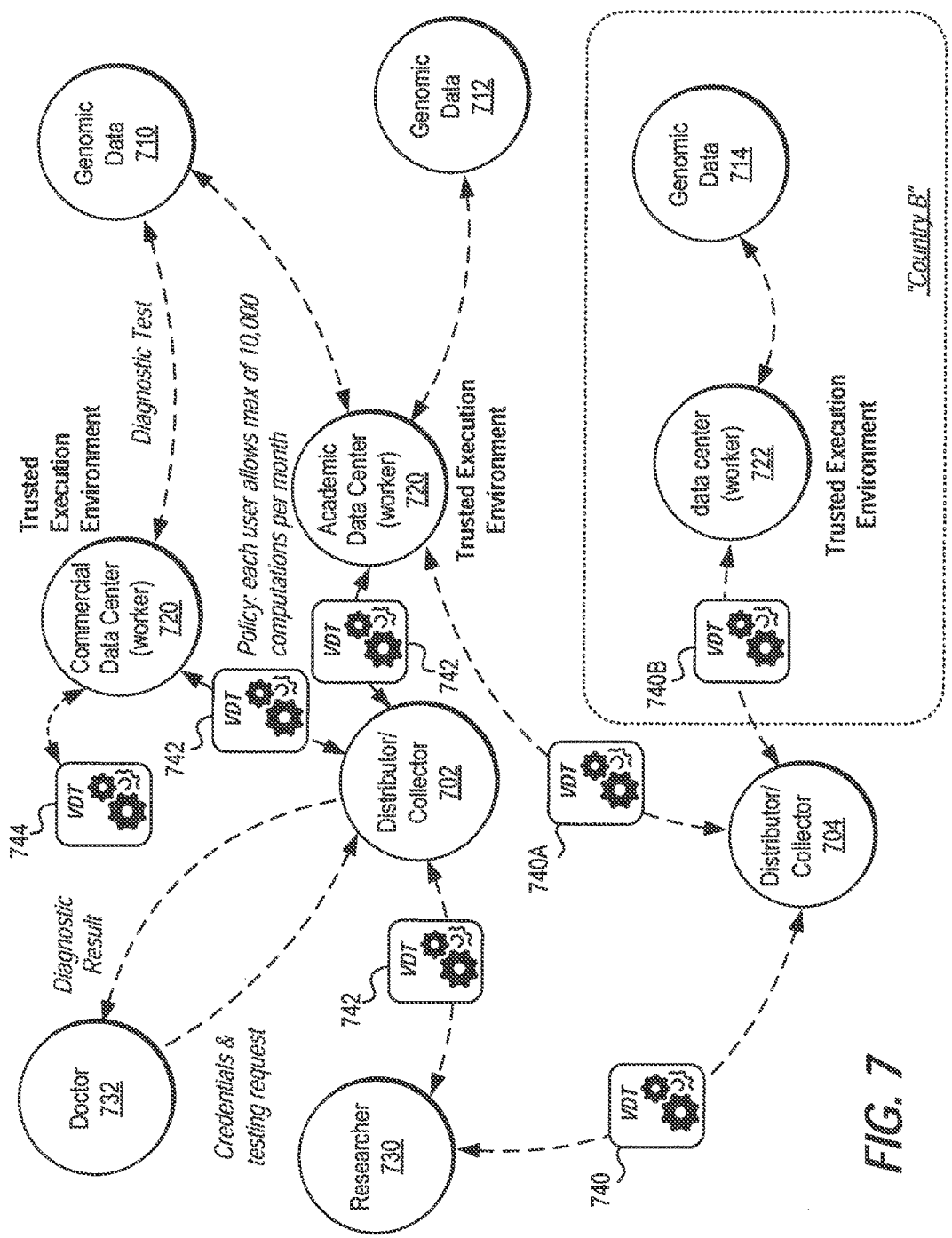
FIG. 7 is a diagram illustrating aspects of another use case, involving genomic data, according to some embodiments.

FIG. 7 is a diagram illustrating aspects of an eighth use case, involving genomic data, according to some embodiments. The system (or "ecosystem") shown is a gene cloud system, such as described in further detail in co-pending U.S. patent application Ser. No. 13/654,349, entitled "Systems And Methods For Protecting And Governing Genomic And Other Information" filed on Oct. 17, 2012, which is hereby incorporated by reference herein in its entirety. In the example gene cloud system shown in FIG. 7, bioinformatics programs, also referred to as Virtual Diagnostic Tests (VDTs), are sent to the genomic data. In other embodiments, some or all of the genomic data is sent to one or more computer systems at which the VDTs are run. At scale, however, it will become more advantageous to have the capability to send the small artifacts (the programs) around to the data, which tends to be very large. According to some embodiments, when the diagnostic programs are sent around to the genetic data, mechanisms are used that (1) ensure that the programs are executed faithfully; (2) audit program execution so that a determination can be carried out (forensically) as to what happened; and (3) protect the results of the computations so that those results can be relied upon.

In FIG. 7, a doctor 732 indicates a desire to have a diagnostic test, embodied in VDT 744, run on a patient's genomic data 710, which may for example be stored at a secure medical data storage facility. The doctor 732 sends a request to a distributor 702. The doctor's request includes credentials (e.g. in the form of the doctor's digital signature), the patient's identifying information, as well as an identification of a diagnostic test program (and/or the diagnostic program itself). The collector/distributor 702 then verifies the doctor's credentials, and, from the patient's identifying information, identifies a commercial data center 720 that includes a Worker node that can carry out the computations on the genomic data in a trusted execution environment. The commercial data center 720 has access to the patient's genomic data 710. According to some examples, the data center 720 may be associated with a secure storage facility in which genomic data 710 is stored. The data center 720 uses the doctor's request to identify VDT 744 as being suitable for the diagnostic test. Alternatively, the VDT 744 could have been identified or specified by either the doctor 732 directly, or by the collector/distributor 702. The Worker node within data center 720 authenticates and validates the request, the VDT 744, and the genomic data 710. The Worker node in center 720 also applies and follows any policies that may be associated with the data, the VDT, or the doctor's request. The diagnostic result from the VDT is then returned to distributor 702 and doctor 732, who incorporates the results into his/her medical opinion.

Note that unlike other distributed computation frameworks, in the gene cloud example system described here, the Worker nodes need not be equivalent, in that they do not typically have access to all of the same raw data. Furthermore, a uniform set of policies is not typically applied to all the computations.

In some embodiments, it may not be feasible to perform a static analysis on a VDT to determine if it respects certain policies. For example: (i) certain environmental variables may be unavailable at the point the program is ingested into the system, but may be available at the Workers that will ultimately execute the programs; (ii) the program may need to be run in order to determine which accesses are actually requested; and/or (iii) the operation of the program may depend on the geographical location at which it is executed.

An example of case (i) is a Worker node that is participating in the trusted execution environment associated with an academic data center 720. The academic data center wishes to limit the use of its computing resources so that a particular user can request only 10,000 computations per month. The counter variables that maintain the number of requests processed per user are known only to that Worker node in center 720, not to the Distributor 702 that is dispatching the job at the request of a researcher 730. The Worker node at center 720 may refuse to service the request if the count is exceeded, and Distributor 702 will not know this in advance.

A second example of case (i) is the situation where a Worker node is able to determine that revealing certain information would compromise the privacy of the individual in question, and therefore refuses to service a request that seeks such information.

An example of case (ii) is where a VDT program 742 is looking for dependencies between two genes, gene A and gene B. The two genes A and B could be part of the same genomic dataset 710, for example, or they could be found in separate datasets such as datasets 710 and 712. For example, if gene A has a particular characteristic, then the program 742 may report which of 17 variants are exhibited by gene B. If gene A does not have the requisite characteristic, then the program reports nothing. In this example, it is not possible to know in advance whether access to gene B is going to be required—this matter is best decided at the Worker node of center 720 as the computation 742 is performed.

As an example of case (iii), researcher 730 is interested in querying many genomic databases in several countries looking for a rare set of conditions. Researcher 730 sends a request to distributor 704 to use a VDT 740 to perform the test. In response, distributor 704 sends certified versions of the VDT, 740A and 740B, to datacenters 720 and 722 respectively. Country B (e.g., Canada) has a health database law that mandates that any queries that return fewer than five results need to be obfuscated to protect privacy. Data center in Country B 722 is used to run the VDT 740B on a genomic dataset 714 in Country B. It will typically not be possible to know in advance how many results will match a given query, so the policies governing randomization/obfuscation are best applied by the individual Worker nodes (in this case a worker node in data center 722) as opposed to a centralized entity.

According to some embodiments, the types of policies that may be associated with a particular data resource include, without limitation, some or all of: access control, privacy control (e.g. limiting the amount of personally identifiable information shared), monetary or non-monetary compensation provisions, identity verification, policies that grant or deny full or partial access depending on identity, purpose, or other attribute of the requestor, and/or policies that grant or deny access depending on the amount of cumulative prior access to a particular resource (e.g. that only allow access a certain number of times, are sensitive to the total amount of information revealed historically, and/or become progressively more restrictive as more of the resource is accessed). An example of the last type of policy is market research data that is collected by a commercial entity. The collected data has value to multiple commercial users, and the stakeholders may not want to give up all the data—retaining the highest resolution/fidelity data for their own use as a competitive advantage. It will be appreciated that while a number of example policies have been listed, any suitable policy or policies could be used.

Some embodiments of the inventive body of work can be used to enable, without limitation, some or all of the following:

Allowing transportable computations that are executed in the environment operated by the owner of the data or derivation on which it operates.

Bringing together derived computations with distributed computations to a set of data stakeholders and reducing the results of these computations to a further result in such a manner that the rights and the policies of the original stakeholders of the data are preserved throughout the computation and potentially beyond the reduction step.

Allowing the computations and the derivation of the data to negotiate the applicable protocols and events that will lead to the result and the construction of the derivation of the result.

Allowing further computations to negotiate with the derivation to produce a transitive derivation that governs the result in reference to a third party.

Figure 8:
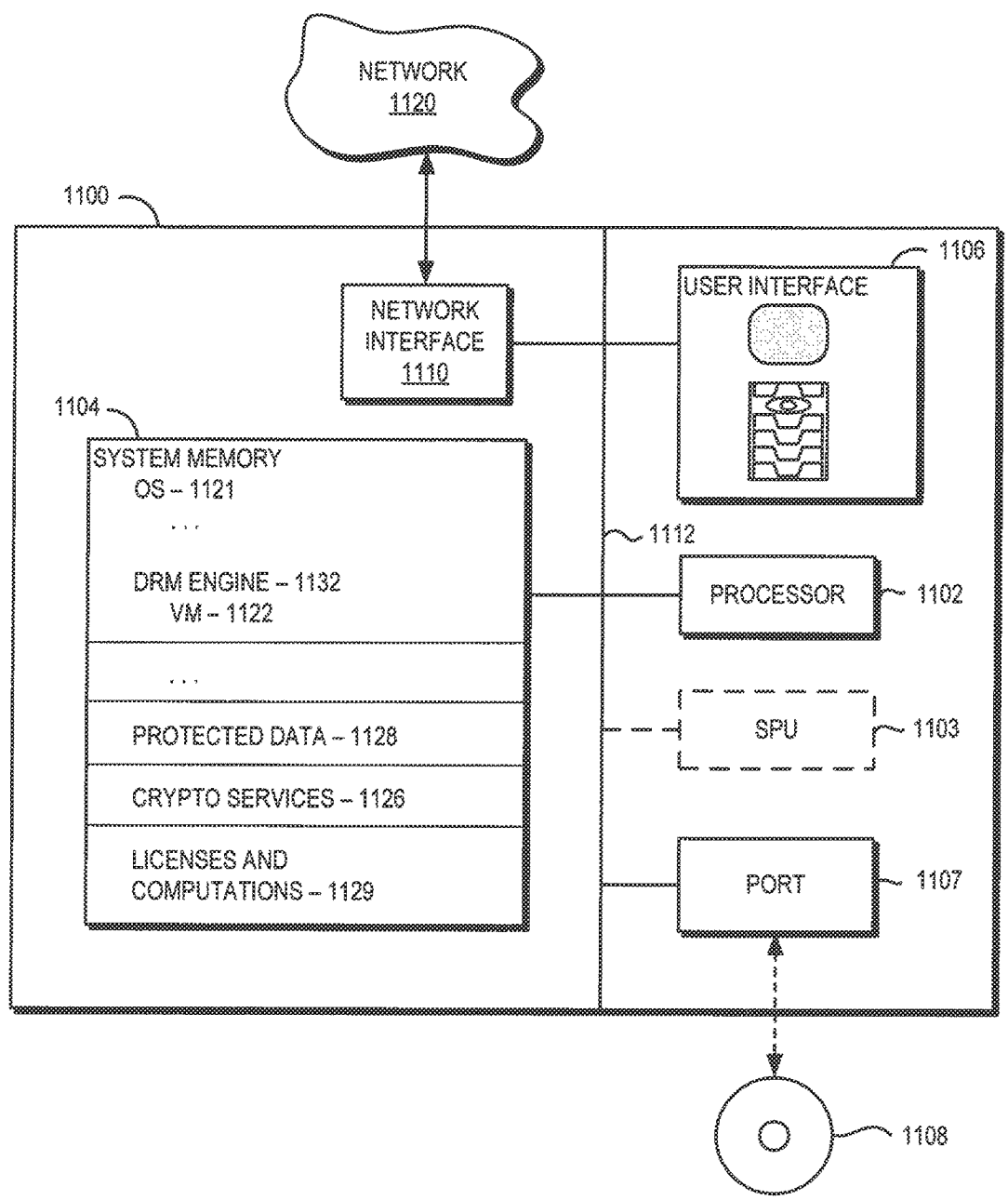
FIG. 8 shows an example of a system that could be used to practice embodiments of the inventive body of work.

FIG. 8 shows an example of a system 1100 that could be used to practice embodiments of the inventive body of work. For example, system 1100 might comprise an embodiment of a device operated by one of more of the entities described above (e.g., Users, Workers, Distributors, Coordinators, Collectors, etc.). System 1100 may, for example, comprise a general-purpose computing device such as a personal computer, smartphone, tablet computer, or network server, or the like. System 1100 will typically include a processor 1102, memory 1104, a user interface 1106, a port 1107 for accepting removable memory 1108, a network interface 1110, and one or more buses 1112 for connecting the aforementioned elements. The operation of system 1100 will typically be controlled by processor 1102 operating under the guidance of programs stored in memory 1104. Memory 1104 will generally include both high-speed random-access memory (RAM) and non-volatile memory such as a magnetic disk and/or flash EEPROM. Some portions of memory 1104 may be restricted, such that they cannot be read from or written to by other components of the system 1100. Port 1107 may comprise a disk drive or memory slot for accepting computer-readable media 1108 such as USB drives, CD-ROMs, DVDs, memory cards, SD cards, other magnetic or optical media, and/or the like. Network interface 1110 is typically operable to provide a connection between system 1100 and other computing devices (and/or networks of computing devices) via a network 1120 such as the Internet or an intranet (e.g., a LAN, WAN, VPN, etc.), and may employ one or more communications technologies to physically make such a connection (e.g., wireless, Ethernet, and/or the like). In some embodiments, system 1100 might also include a processing unit 1103 that is protected from tampering by a user of system 1100 or other entities. For example, in some embodiments an SPU 1103 such as described in commonly-assigned U.S. Pat. No. 7,430,585 ("the '585 patent") and/or U.S. Pat. No. 5,892,900 ("the '900 patent") could be used. Such a secure processing unit can help enhance the security of sensitive operations such as key management, signature verification, and other aspects of the systems and methods described elsewhere herein.

As shown in FIG. 8, memory 1104 of computing device 1100 may include data 1128 and a variety of programs or modules for controlling the operation of computing device 1100. For example, memory 1104 will typically include an operating system 1121 for managing the execution of applications, peripherals, and the like. Memory 1104 also may include a variety of applications, such as an application for ingesting protected data, performing computations on such data, and/or the like; a DRM engine 1132 or other policy enforcement application for enforcing policy restrictions as described elsewhere herein; and/or one or more programs for performing the operations described above with respect to FIGS. 1-7. As described elsewhere herein, policy enforcement engine 1132 may comprise, interoperate with, and/or control a variety of other modules, such as a virtual machine for executing control programs, a protected database for storing sensitive information, and/or one or more cryptographic modules 1126 for performing cryptographic operations such as encrypting and/or decrypting content, computing hash functions and message authentication codes, evaluating digital signatures, and/or the like. Memory 1104 will also typically include protected content 1128 and associated licenses and computations 1129, as well as cryptographic keys, certificates, and the like (not shown). In certain embodiments, the systems and methods described herein could, for example, be used in connection with security and/or digital rights management ("DRM") technologies such as those described in commonly assigned, co-pending U.S. patent application Ser. No. 11/583,693, filed Oct. 18, 2006, and published as Publ. No. 2007/0180519 A1 ("the '693 application"), U.S. Pat. No. 5,892,900, and U.S. Pat. No. 6,157,721 ("the '721 patent"), and/or service orchestration or DRM technologies such as those described in commonly assigned U.S. Pat. No. 8,234,387 ("the '387 patent") (the contents of the '693 application and the '585 patent, '900 patent, '721 patent, and '387 patent hereby being incorporated by reference in their entireties). For example, DRM software and systems such as those described in the '693 application, the '387 patent, and/or the '900 patent could be used in some embodiments to facilitate the expression and enforcement of rules, rights, and policies of the type described herein. In will be appreciated, however, that any other suitable security and/or policy-enforcement software, systems, and/or mechanisms could be used instead or in addition.

One of ordinary skill in the art will appreciate that the systems and methods described herein can be practiced with computing devices similar or identical to that illustrated in FIG. 8, or with virtually any other suitable computing device, including computing devices that do not possess some of the components shown in FIG. 8 and/or computing devices that possess other components that are not shown. Thus it should be appreciated that FIG. 8 is provided for purposes of illustration and not limitation, and that the systems and methods disclosed herein are not inherently related to any particular computer, electronic control unit, or other apparatus and may be implemented by any suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network. Software embodiments may be implemented as a computer program product that comprises a storage medium configured to store computer programs and instructions, that when executed by a processor, are configured to cause the processor to perform a method according to the instructions. In certain embodiments, the storage medium may take any form capable of storing processor-readable instructions; examples of which include, without limitation, non-transitory storage media embodied by a compact disk, digital-video disk, a magnetic tape, a magnetic disk, flash memory, integrated circuits, or any other non-transitory digital processing apparatus memory device.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein, but may be modified within the scope and equivalents of the appended claims.

What is claimed is:

1. A method for performing distributed computing tasks using distributed digital data resources having differing associated rules, the method comprising:
   receiving, from a distributing entity by a first distributed worker node, a first computing sub-task to be performed by the first distributed worker node using a first digital data resource, the first computing sub-task being a divided sub-task of a plurality of divided sub-tasks associated with a computing task, the first digital data resource being associated with a first set of rules that correspond to one or more conditions for accessing the first digital data resource;
   determining, by the first distributed worker node, that the first distributed worker node has at least partial access rights to the first digital data resource, the at least partial access rights being independent of the access rights of the distributing entity;
   performing, by the first distributed worker node, the first computing sub-task to generate a first partial result based on the determination that the first distributed worker node has at least partial access rights to the first digital data resource; and
   sending, from the first distributed worker node to a collector entity, the first partial result.

2. The method of claim 1, wherein the first set of rules further correspond to one or more computations that operate on the first digital data resource.

3. The method of claim 1, wherein the distributing entity and the collector entity comprise the same entity.

4. The method of claim 1, wherein the first set of rules are determined at least in part by one or more stakeholders in the first digital data resource.

5. The method of claim 1, wherein the distributing entity has less access rights to the first digital data resource than the at least partial access rights of the first distributed worker node.

6. The method of claim 1, wherein the distributing entity is not able to set data access policies observed by the first distributed worker node.

7. The method of claim 1, wherein the distributing entity is not able to set data access policies associated with the first digital data resource.

8. The method of claim 1, wherein the first set of rules comprises rules selected from a domain of possible rules that are not determined by the distributing entity.

9. The method of claim 1, wherein the first set of rules are associated with a first set of computations that operate upon the first digital data resource in order to provide a specific view of the first digital data resource.

10. The method of claim 9, wherein at least one computation of the first set of computations is associated with the first digital data resource and with a first user in order to limit the first user's access to information contained in the first digital data resource by requiring that the at least one computation be applied to the first digital data resource before revealing the information to the first user.

11. The method of claim 9, wherein the association between the first set of rules with the first set of computations is made by creating a digitally signed document comprising a paring of a unique representation of the first digital data resource and a unique representation of the first set of computations to be associated with the first digital data resource.

12. The method of claim 1, wherein the first digital data resource comprises medical information.

13. The method of claim 12, wherein the medical information comprises genomic data relating to a plurality of individuals.

14. The method of claim 12, wherein the first set of rules comprises rules corresponding to conditions that protect patient privacy.

15. The method of claim 12, wherein the first digital data resource comprises medical information relating to a plurality of patients including a first patient and a second patient, the first set of rules corresponding to access conditions that are different for medical information relating to the first patient than for medical information relating to the second patient.

16. The method of claim 5, wherein at least some of the first set of rules are set at least in part by one or more of the plurality of parents.

17. The method of claim 1, wherein the method further comprises:
   generating, by the first distributed worker node, a second computing sub-task to be performed by a second distributed worker node using a second digital data resource, the second computing-sub task being a sub-task of the first computing sub-task, the second digital data resource being associated with a second set of rules that correspond to one or more conditions for accessing the second digital data resource; and
   sending, from the first distributed worker node to the second distributed worker node, the second computing sub-task.

18. The method of claim 17, wherein the method comprises receiving, from the second distributed worker node, a second partial result response to the second computing sub-task.

19. The method of claim 18, wherein generating the first partial result is based in part on the second partial result.

20. The method of claim 17, wherein the one or more conditions for accessing the first and second digital data resources corresponding to the first and second set of rules differ from each other.

21. The method of claim 17, wherein the first distributed worker node does not have access to the second digital data resource and the second distributed worker node does not have access to the first digital data resource.

22. The method of claim 17, wherein the first and second digital data resources are located in geographically separate locations.

23. The method of claim 22, wherein the first and second digital data resources are located in different countries.

* * * * *